United States Patent [19]

Isenberg

[11] 4,138,881

[45] Feb. 13, 1979

[54] RESISTOR-TYPE SOLID ELECTROLYTE OXYGEN SENSOR

[75] Inventor: Arnold O. Isenberg, Pittsburgh, Pa.

[73] Assignee: Westinghouse Electric Corp., Pittsburgh, Pa.

[21] Appl. No.: 874,187

[22] Filed: Feb. 1, 1978

[51] Int. Cl.² ............................................. G01N 27/12
[52] U.S. Cl. .................... 73/27 R; 23/254 E; 204/195 S; 338/34
[58] Field of Search ............ 73/27 R; 204/1 T, 195 S; 23/254 E; 338/34

[56] References Cited

U.S. PATENT DOCUMENTS

| Re. 28,792 | 4/1976 | Ruka | 204/195 S |
|---|---|---|---|
| 3,479,257 | 11/1969 | Shaver | 338/34 X |
| 3,503,809 | 3/1970 | Spacil | 204/195 S |
| 3,558,280 | 1/1971 | Panson | 23/254 E |
| 3,959,764 | 5/1976 | Allman | 338/34 |
| 3,989,614 | 11/1976 | Tien | 204/195 S |
| 4,068,021 | 1/1978 | Allman | 338/34 X |
| 4,077,775 | 3/1978 | Lacroix | 338/34 X |
| 4,080,276 | 3/1978 | Bode | 204/195 S |

FOREIGN PATENT DOCUMENTS

| 870223 | 5/1971 | Canada | 204/195 S |
| 2454339 | 5/1975 | Fed. Rep. of Germany | 204/195 S |

*Primary Examiner*—Richard R. Kucia
*Attorney, Agent, or Firm*—M. P. Lynch

[57] ABSTRACT

An oxygen sensor consisting of an oxygen ion conductive solid electrolyte member coated with a porous cermet structure which exhibits a metallic and ceramic skeleton develops a resistance change in response to a change in oxygen partial pressure at elevated temperatures. The resistance change, when coupled to an electrical circuit, provides an electrical indication of the oxygen partial pressure of the atmosphere contacting the oxygen sensor.

5 Claims, 3 Drawing Figures

RESISTOR-TYPE SOLID ELECTROLYTE OXYGEN SENSOR

BACKGROUND OF THE INVENTION

The composition and application of solid electrolyte electrochemical cells as oxygen sensors have been described in detail in prior art publications including reissue patent Re. 28,792 which is assigned to the assignee of the present invention and is incorporated herein by reference.

The operation of many conventional solid electrolyte oxygen sensors requires the presence of a reference oxygen source which typically is either a gas or a metal/metal oxide mixture. The necessity for an oxygen reference increases the design complexity and cost of many conventional solid electrlyte oxygen sensors.

Resistor-type oxygen sensors are also well known in the art. The resistor-type oxygen sensor typically consists of a semiconducting metal-oxide which experiences a change in the electronic structure caused by a change in the stoichiometry of the oxide. A reducing atmosphere causes oxygen deficiencies in the metal-oxide lattice of the conventional resistor-type oxygen sensor. A free oxygen containing atmosphere on the other hand can cause excess oxygen in the lattice. In other words, the oxygen concentration in the surrounding atmosphere can produce mass changes in the conventional resistor-type oxygen sensor. This results in insufficient response times and accuracy.

The application of a mixed valence oxide compound as a resistor-type solid state oxygen sensor is disclosed in detail in U.S. Pat. No. 3,558,280, entitled "Solid State Oxygen Gauge", issued Jan. 26, 1971, assigned to the assignee of the present invention and incorporated herein by reference.

SUMMARY OF THE INVENTION

There is disclosed herein with reference to the accompanying drawings a resistor-type solid state oxygen sensor consisting of an oxygen ion conductive solid electrolyte member of a composition similar to that disclosed in the above-identified reissue patent, and a porous cermet layer having both a metallic skeleton and a ceramic skeleton, wherein the ceramic skeleton supports oxygen ion conductivity at elevated temperatures.

The particular selection of the ceramic and metallic compositions for the cermet layer as well as the selection of the material composition for the solid electrolyte member is a matter of design choice having had the benefit of the following discussion.

DESCRIPTION OF THE DRAWINGS

The invention will become more readily apparent from the following exemplary description in connection with the accompanying drawings.

DESCRIPTION OF THE PREFERRED EMBODIMENT

While the following discussion will employ a specific composition for the solid electrolyte member and the cermet layer to provide a specific disclosure of an operating oxygen sensor, it is apparent to those skilled in the art that oxygen ion conductive solid electrolyte materials other than zirconia can be employed. For instance, oxygen ion conducting ceramics include ceria, thoria, hafnia, magnesia and some titanates. In addition to platinum, other suitable electron conductive metals include silver, gold and other noble metals of the platinum group.

Figure 1:
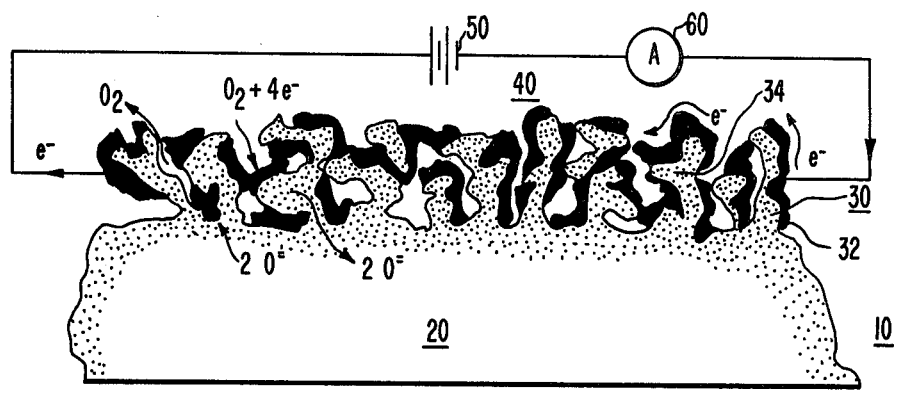
FIG. 1 is a sectioned schematic illustration of resistor-type solid electrolyte oxygen sensor incorporating the inventive concept.

Referring to FIG. 1, a typical embodiment of the resistor-type solid electrolyte oxygen sensor 10 is sectionally illustrated to consist of an oxygen ion conductive solid electrolyte member 20 and a cermet layer 30 in intimate contact therewith. The sensor 10 forms a resistive element in the electrical circuit 40 which includes a DC source 50 and an ammeter 60 connected in series with the cermet layer 30. The cermet layer 30 is illustrated as a porous structure consisting of a metallic skeleton 32 and a ceramic skeleton 34. For the purposes of discussion, it will be assumed that the metallic skeleton 32 consists of platinum and the ceramic skeleton 34 consists of zirconia. The oxygen ion conductive solid electrolyte member 20, of which there are numerous suitable material compositions as described in the above-identified reissue patent, is typically illustrated in FIG. 1 to consist of yttria stabilized zirconia.

At elevated temperatures, i.e., over 500° C., the zirconia becomes an oxygen ion conductor. In the presence of oxygen in the surrounding atmosphere A, the porosity of the cermet layer 30 provides intimate contact of the oxygen with the solid electrolyte member 20. In the presence of oxygen, at suitable elevated operating temperatures, a DC current is permitted to flow in the circuit 40.

In order to let oxygen enter and exit the solid electrolyte member 20, electrons must be provided and accepted. This electronic conductivity is accomplished by the continuous metal phase of metallic skeleton 32 that is in intimate contact with the ceramic skeleton 34 of the cermet layer 30.

The mode of operation of the sensor 10 is as follows. The application of a DC voltage to the sensor will result in a current that flows through the metallic skeleton 32 at all times and temperatures. If the sensor 10 is heated to a temperature, i.e., over 500° C., an additional oxygen-ionic current will flow through the ceramic skeleton 34 of the sensor 10 if oxygen is present in the atmosphere, thus reducing the total resistance of the sensor 10. Variations in the oxygen concentration of the surrounding atmosphere will result in resistance variation because gaseous oxygen is needed to create the oxygen-ion flow in the ceramic skeleton 34 of the sensor 10.

Figure 2:
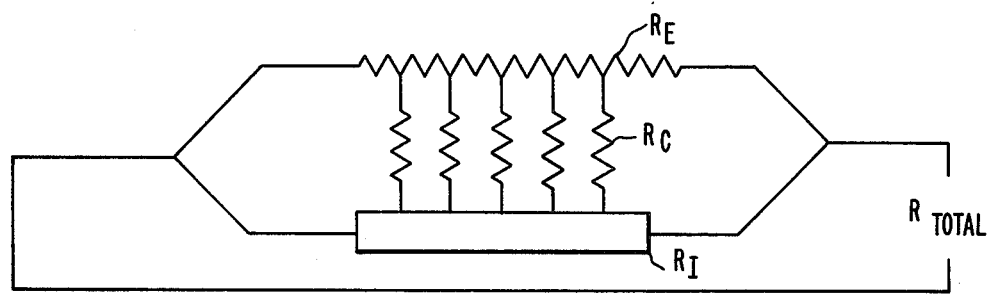
FIG. 2 is an electrical schematic equivalent circuit of the embodiment of FIG. 1.

The oxygen sensor 10 effectively represents two parallel resistors, as schematically illustrated in FIG. 2. One resistance $R_E$ corresponds to the electron conductor while the second resistance $R_I$ corresponds to the oxygen-ion conductor. The resistance mix, as schematically illustrated in FIG. 2, extends over the entire length of the oxygen sensor 10 in which there is intimate contact between the solid electrolyte member 20 and the cermet layer 30.

Two major considerations in selecting the material compositions for the oxygen sensor are the material compatability of the materials, namely, that they do not experience chemical changes in the oxygen atmosphere at the elevated temperature, and secondly that the resistance of the oxygen-ion conductor is comparable to that of the electronic conductor.

If for instance, the metallic skeleton 32, i.e., platinum, in the cermet layer 30 would form a very low resistance continuous conductor, the change in the ionic current flow with varying oxygen concentration would not be noticeable. The distribution of the metal skeleton 32 in the cermet layer 30 assures a significantly high resistance $R_E$ such that a "balanced" resistance condition is formed between the electronic resistance $R_E$ and the ionic resistance $R_I$. Thus, in an elongated cermet layer 30, as illustrated in FIG. 1, wherein the electrical leads of the circuit 40 are connected to either end of the elongated cermet layer 30, the effective electronic resistance, $R_E$ formed by the metallic skeleton 32, is comparable to the ionic resistance $R_I$ formed by the ceramic skeleton 34.

Figure 3:
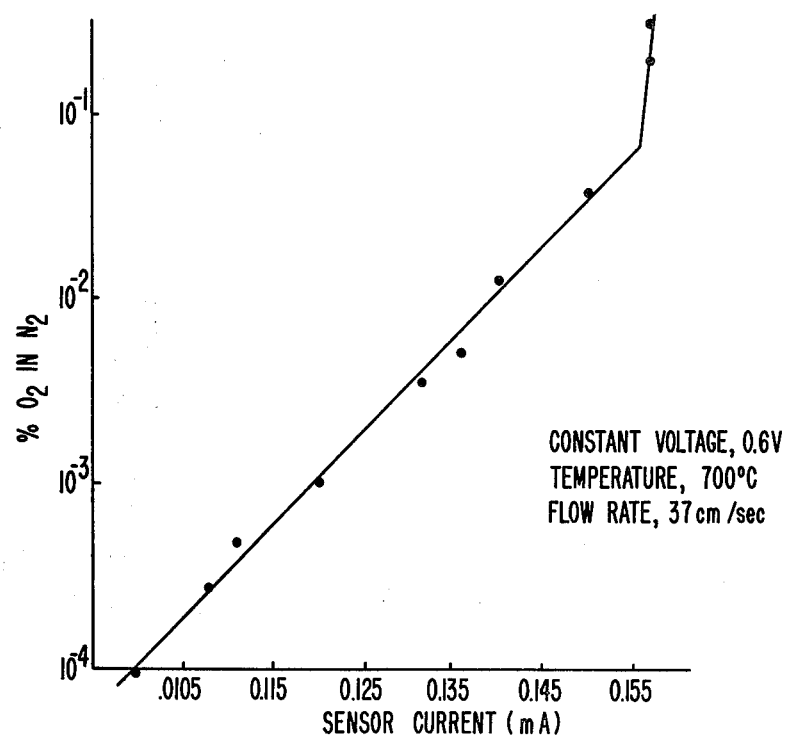
FIG. 3 is a plot of percent oxygen in nitrogen versus oxygen sensor current illustrating the operation of the embodiment of FIG. 1.

The operation of the cermet layer/solid electrolyte oxygen sensor 10 of FIG. 1 is illustrated in FIG. 3. The bend in the curve at about 0.1% oxygen concentration indicates that excess oxygen is available in the pores of the cermet layer 30 so that no further significant increase in the direct current produced by a decrease in resistance can be expected via the solid electrolyte member 20. The location of the bend in the curve depends on the porosity of the cermet layer 30 and the sensor operating temperature. The higher the operating temperature, the better the sensitivity at the higher oxygen concentration ranges. Typically, however, the sensor 10 has been shown to operate effectively in atmospheres having less than 1% free oxygen content.

I claim:

1. An oxygen measuring apparatus, comprising, an oxygen sensor means including an oxygen ion conductive solid electrolyte member and a porous cermet layer disposed in intimate contact with the surface of said oxygen ion conductive solid electrolyte member, said cermet layer including a metallic skeleton and a ceramic skeleton, said oxygen sensor exhibiting a change in resistance in response to a change in the oxygen partial pressure of a gas environment contacting said oxygen sensor, and circuit means connected to said cermet layer to manifest said change in resistance as an indication of the oxygen partial pressure of a gas environment contacting said oxygen sensor.

2. An oxygen measuring apparatus as claimed in claim 1 wherein said ceramic skeleton consists of zirconia and said metallic skeleton consists of platinum.

3. An oxygen measuring apparatus as claimed in claim 1 wherein said circuit means includes a DC voltage source which is connected to said oxygen sensor means to produce a current flow through said metallic skeleton, said ceramic skeleton supporting oxygen ion current flow in response to the presence of oxygen in a gas environment contacting said oxygen sensor means, said oxygen ion current flow reducing the total resistance of said oxygen sensor means.

4. An oxygen measuring apparatus as claimed in claim 1 wherein said ceramic skeleton is of a material to support oxygen ion current flow.

5. An oxygen measuring apparatus as claimed in claim 1 wherein the distribution of the metallic skeleton in said cermet layer is such as to provide a balanced resistance condition between the electronic resistance and the ionic resistance of said oxygen sensor.